United States Patent [19]

Omley

[11] Patent Number: 4,484,918
[45] Date of Patent: Nov. 27, 1984

[54] METHOD AND TOOL FOR EXPANDING A RESILIENT RING FOR SLIDING OVER AND POSITIONING ON A PENIS FOR ANCHORING A RESILIENT CATHETER THERETO

[76] Inventor: Herbert A. Omley, P.O. Box L-2, Wickenburg, Ariz. 85358

[21] Appl. No.: 516,927

[22] Filed: Jul. 25, 1983

Related U.S. Application Data

[62] Division of Ser. No. 332,938, Dec. 21, 1981, Pat. No. 4,416,275.

[51] Int. Cl.³ .............................................. A61F 5/44
[52] U.S. Cl. ................................................... 604/349
[58] Field of Search ............... 128/303 A, 127, 17, 128/326, 345, 303.11, 79, 760; 433/11, 18; 24/265 EE; 604/346, 347, 349–353; 4/144.3

[56] References Cited

U.S. PATENT DOCUMENTS

| | | | |
|---|---|---|---|
| 823,877 | 6/1906 | Kellog | 128/326 |
| 1,273,480 | 7/1918 | Griffith . | |
| 1,328,624 | 1/1920 | Graham | 128/345 |
| 1,383,944 | 7/1921 | Hart | 128/79 |
| 2,379,346 | 6/1945 | Farrell | 128/295 |
| 2,447,474 | 8/1948 | Hammond | 128/319 |
| 2,528,508 | 11/1950 | Gabel | 128/303 |
| 2,601,547 | 6/1952 | Minock | 128/326 U X |
| 2,699,781 | 1/1955 | Koch | 128/295 |
| 2,764,160 | 9/1956 | Alexander et al. | 128/326 |
| 2,844,144 | 7/1958 | Perdue | 29/235 |
| 3,138,160 | 6/1964 | Stoutenburgh | 128/295 |
| 3,409,013 | 11/1968 | Berry | 128/326 |
| 3,421,507 | 1/1969 | Gresham | 604/349 |
| 3,526,227 | 9/1970 | Appelbaum | 128/295 |
| 3,631,857 | 1/1972 | Maddison | 604/349 |
| 3,648,700 | 3/1972 | Warner | 604/349 |
| 3,750,652 | 8/1973 | Sherwin | 128/17 |
| 4,154,242 | 5/1979 | Termanini | 128/349 |
| 4,187,851 | 2/1980 | Hauser | 604/356 |
| 4,232,675 | 11/1980 | Merdahl | 604/353 |
| 4,261,089 | 4/1981 | Taylor | 29/235 |
| 4,370,979 | 2/1983 | Erickson | 128/303 A |
| 4,378,018 | 3/1983 | Alexander et al. | 604/350 |

*Primary Examiner*—C. Fred Rosenbaum
*Assistant Examiner*—J. L. Kruter
*Attorney, Agent, or Firm*—Warren F. B. Lindsley

[57] ABSTRACT

A method and tool for applying a self-carried urine receptacle snugly on the penis of a human which comprises an elastic ring expanded to slide over the shaft of the penis without contacting it, relaxing the ring and causing it to return to its normal position, and sliding the funnel shaped end of a resilient catheter over the penis and ring with the catheter gripping the outside of the ring in a leadproof manner.

4 Claims, 11 Drawing Figures

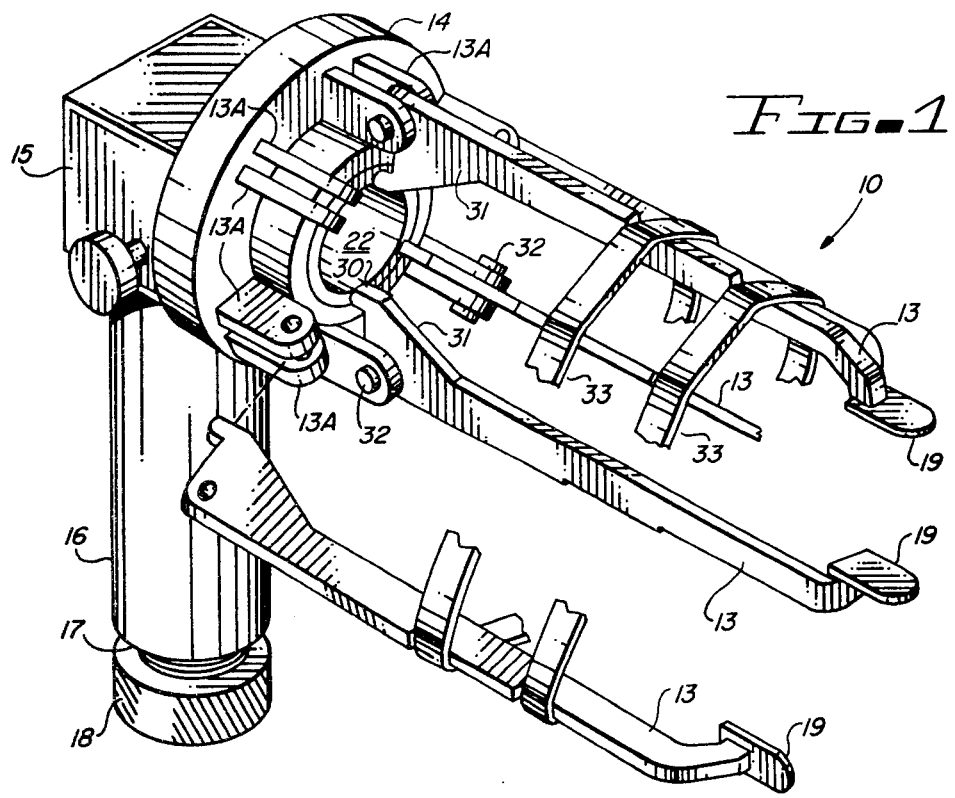
FIG-1
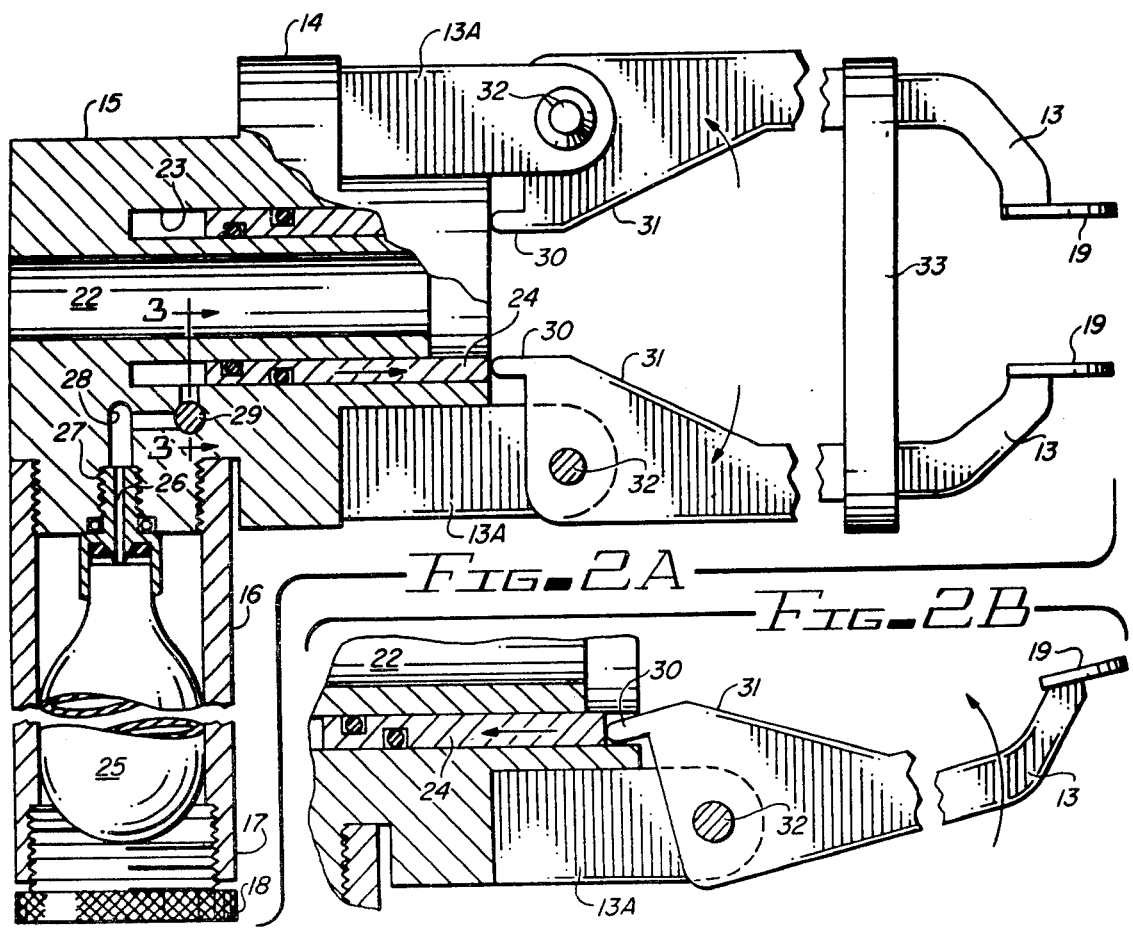
FIG-2A
FIG-2B

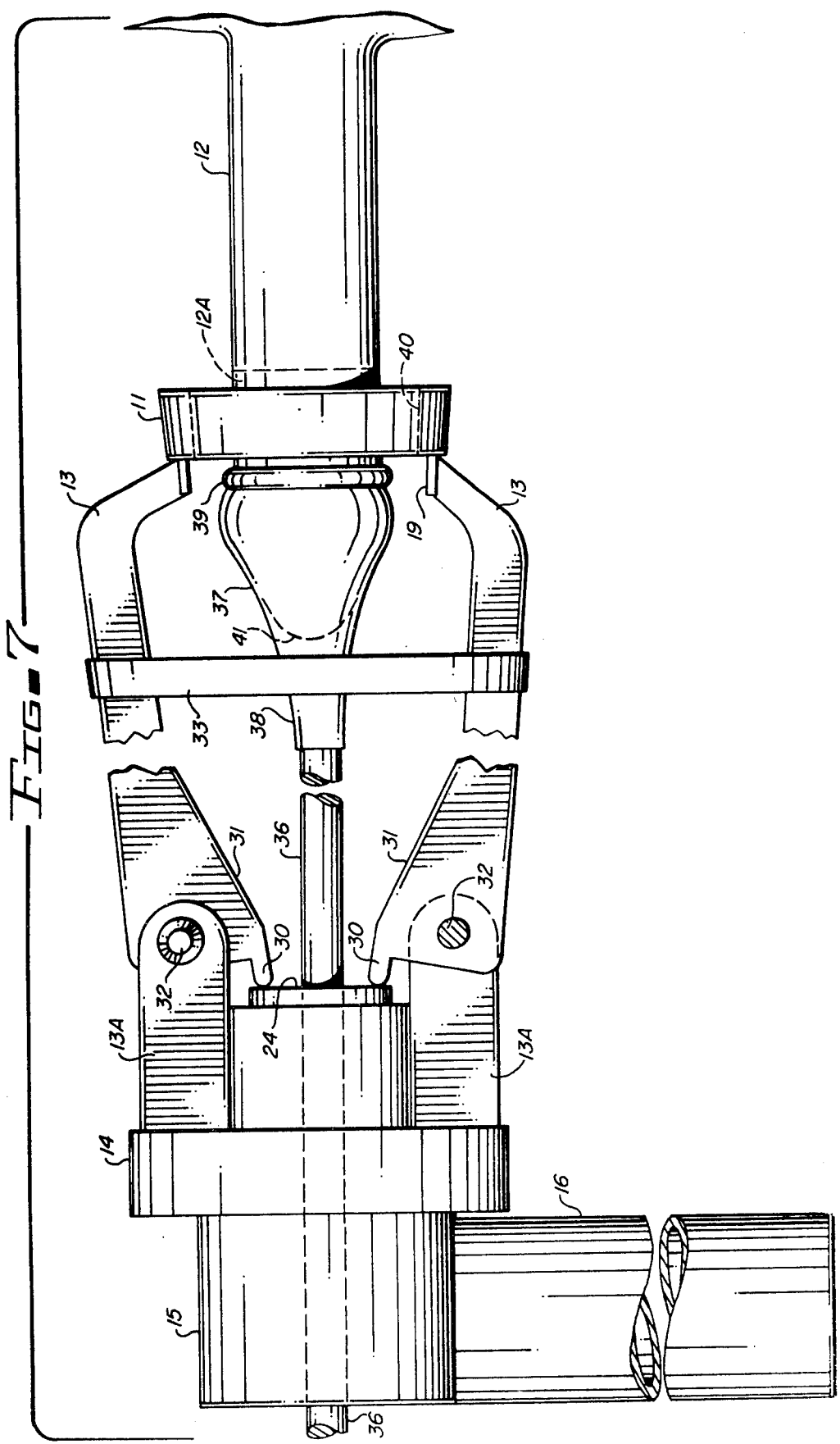

METHOD AND TOOL FOR EXPANDING A RESILIENT RING FOR SLIDING OVER AND POSITIONING ON A PENIS FOR ANCHORING A RESILIENT CATHETER THERETO

BACKGROUND OF THE INVENTION

This application is a division of U.S. patent application Ser. No. 332,938, filed Dec. 21, 1981, and entitled APPARATUS FOR APPLYING A URINE RECEPTACLE TO A MALE, by the same inventor now U.S. Pat. No. 4,416,275.

This invention relates to apparatus and objects to be used therewith for applying self-carried urine receptacles snugly on the penis of a human with little or no danger of involuntary leakage, whether or not the user is ambulatory or confined to his bed.

FIELD OF THE INVENTION

This invention is particularly directed to an elastic annular expandable ring for use with a urine receptacle and a novel appliance for expanding the ring and applying it to the penis for use in securely affixing a urine receptacle to a user.

DESCRIPTION OF THE PRIOR ART

Although urinary weaknesses have occurred in the male, particularly the young and the old, probably from the beginning of time, it is only recently that a serious attempt has been made to aid the wearer of a urine receptacle in maintaining a leakproof arrangement, whether he is ambulatory or bed confined.

U.S. Pat. Nos. 1,273,480; 2,379,346; and 2,699,781 all teach penile type collectors which employ drain valves. U.S. Pat. No. 1,273,480 also teaches the use of a reinforcing band adapted to encircle the urine receptacle at some point remote from the end of the penile gland.

U.S. Pat. Nos. 3,138,160 and 3,526,227 teach the use of a resilient structure for encircling the outside of urine receptacles at some point remote from the end of the penile gland to resiliently engage and retain these receptacles in place.

U.S. Pat. Nos. 3,409,013 and 3,750,650 disclose instruments for producing expansion-retraction movements.

U.S. Pat. No. 4,154,242 discloses a catheter for effecting complete drainage of a bladder.

U.S. Pat. Nos. 2,447,474 and 2,528,508 disclose rubber ring expandable tools.

None of these patents disclose a satisfactory means for attaching a suitable urine receptacle to a male patient which is leakproof and completely functional, whether the user is ambulatory or bed confined.

SUMMARY OF THE INVENTION

In accordance with the invention claimed, a new and improved urinary appliance and device for applying it to a male user is provided which assures the user of a substantially leakproof arrangement and which can be readily applied with less difficulty than similar appliances of the prior art.

It is, therefore, one object of this invention to provide a device or apparatus which may be conveniently applied and used by male incontinents, either ambulatory or bedridden, which is substantially leakproof.

Another object of this invention is to provide a new and improved annular resilient ring for encircling and firmly gripping the penis over which the mouth of a urine receptacle may be securely affixed in a leakproof manner.

A further object of this invention is to provide a new and improved tool for use in grabbing and holding the glans penis while applying an improved annular ring to the shaft of the penis in such a manner that the adhesive surface of the inner periphery of the ring is kept from contacting the undesirable portions of the body.

A still further object of this invention is to provide a new and improved ring expander for use with a tool for holding the glans penis.

A still further object of this invention is to provide a readily usable urinary appliance and tool for application which may be used with confidence in obtaining a leakproof arrangement.

Additional objects and advantages of the invention will become apparent as the following description proceeds and the features of novelty which characterize the invention will be pointed out with particularity in the claims annexed to and forming a part of this specification.

BRIEF DESCRIPTION OF THE DRAWINGS

The present invention may be more readily described with reference to the accompanying drawings in which:

FIG. 1 is a perspective view of a resilient ring expanding apparatus constructed in accordance with the invention;

FIG. 2A is a partial broken away cross-sectional view of FIG. 1 showing the fluid mechanism for actuating the device;

FIG. 2B is a partial cross-sectional view of one of the fingers of the apparatus shown in FIGS. 1 and 2 in its retracted position;

FIG. 7 is a partial perspective view of the apparatus of FIG. 1, ring of FIG. 4 and tool of FIG. 5 being used in applying a resilient ring to a male.

DESCRIPTION OF THE PREFERRED EMBODIMENT

Figure 3:
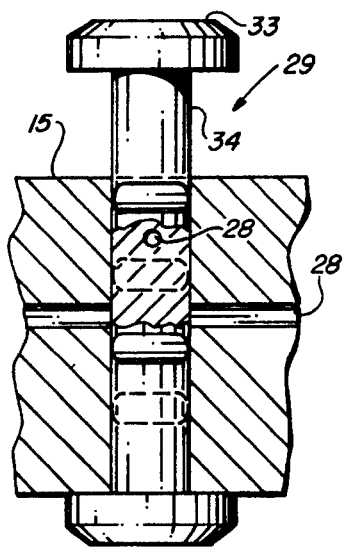
FIG. 3 is a cross-sectional view of FIG. 2A taken along the line 3—3.
Figure 4:
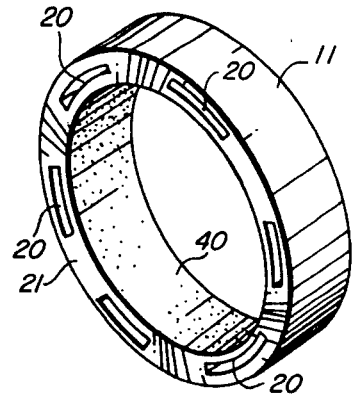
FIG. 4 is a perspective view of an expandable ring for applying to the shaft of the penis of a user with the disclosed apparatus.

Referring more particularly to the drawings by characters of reference, FIGS. 1–3 disclose an instrument or apparatus 10 for applying a resilient, elastic, expandable ring 11, as shown in FIG. 4, to a shaft 12 (FIGS. 6A–6D) of the penis of a human user. This instrument comprises a plurality of arms or jaws 13, each spacedly and pivotally mounted on ears or arms 13A extending laterally from and around the flat surface of a circular supporting disk 14. Disk 14 comprises a part of an integral housing 15, part of which is mounted to extend substantially perpendicular to the direction of jaws 13 and forming a grip or handle 16 of the apparatus for the convenience of a user.

As noted from FIGS. 1 and 2A of the drawings, handle 16 of housing 15 comprises a hollow configuration arranged to be closed at its open end 17 by a plug 18 which threadedly engages the interior of the open end 17 of the handle.

The opposite or free ends of jaws 13 are provided with pads or fingers 19 which are arranged to extend into cooperating grooves or slots 20 spacedly formed in end 21 of ring 11, as shown in FIG. 4. Fingers 19 are mounted so as to extend parallel with the longitudinal axis of disk 14 on which the jaws are mounted. Thus, in the retracted position of fingers 19, they are arranged to extend into slots 20 of ring 11 to firmly grip ring 11 so that it may be expanded by apparatus 10.

It should be noted from FIGS. 1 and 2A of the drawings that an opening 22 is arranged to extend through housing 15, the longitudinal axis of which is coaxially aligned with the longitudinal axis of disk 14 and jaws 13.

A further cylindrical opening 23 is arranged to extend coaxially with and around the periphery of opening 22 in which a ring shaped piston 24 is mounted for reciprocal movement.

As shown in FIG. 2A, a canister 25 of fluid under pressure, such as air or any other suitable gas, is replaceably mounted in the open end 17 of handle 16 which, when mounted therein, places the gas under pressure in the canister in communication with the left end of opening 23 through a passageway 26 in plug 27 and a passageway 28 in housing 15.

A slidable valve means 29 mounted in passageway 28, shown in more detail in FIG. 3, controls the flow of gas under pressure from canister 25 to the left end of piston 24, as shown in FIG. 2A. This valve when open, as shown in FIG. 3, connects gas under pressure in passageway 28 to the left side of piston 24 to move it to the right. This movement of piston 24 engages and biases prongs 30 on the ends 31 of jaws 13 to cause each of them to pivot about their pins 32. This action moves fingers 19 generally radially away from each other at their other ends against the biasing action of a suitable means which, for example, may comprise a pair of rubber bands 33 which encompass the outer periphery of jaws 13 and the biasing effect of ring 11.

When the pressure is reduced or relieved in passageway 28 upon the movement of slide valve 29 to a position opposite to that shown in FIG. 3 by finger pressure on the end 33 of shaft 34 moving end 33 toward housing 15, the gas in cylinder or opening 23 is released to the atmosphere along one end of the stem of valve 29 in a well known manner.

The biasing effect of rubber bands 33 and ring 11 then moves jaws 13 toward each other. This action pivots jaws 13 about their pins 32 causing prongs 30 of jaws 13 to move piston 24 to the left, as shown in FIG. 2B.

Thus, through the use of slide valve 29, fluid pressure may be applied to instrument 10 to spread the free ends of jaws 13 apart and upon the release of that pressure, the rubber bands 33 and ring 11 return piston 24 to its unbiased position and fingers 19 and jaws 13 to their unbiased position, shown in FIG. 2A.

Figure 5:
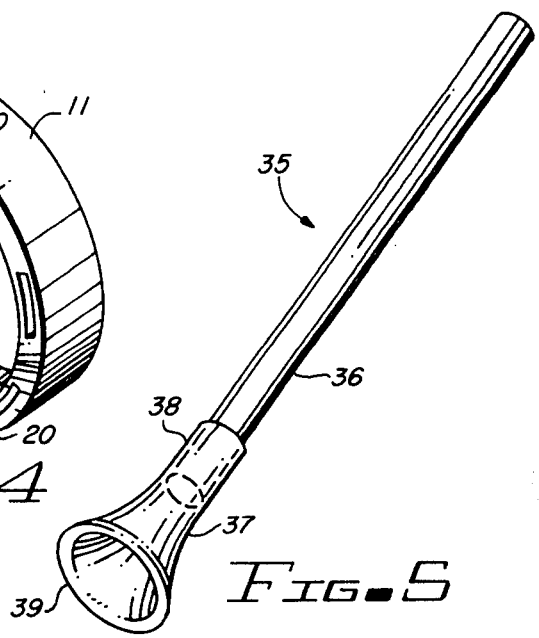
FIG. 5 is a perspective view of a tool for attaching to and holding the glans penis of a user.

In order to use instrument 10 in applying a urinary receptacle to a male, a suitable tool, such as a glans grabber 35 shown in FIG. 5, is employed. This tool comprises a rod 36 to one end of which is applied a resilient funnel-shaped member 37. The spout end 38 of member 37 is telescopically fitted over one end of rod 36. The flared end 39 of the funnel-shaped member 37 is rolled over on itself.

Figure 6A:
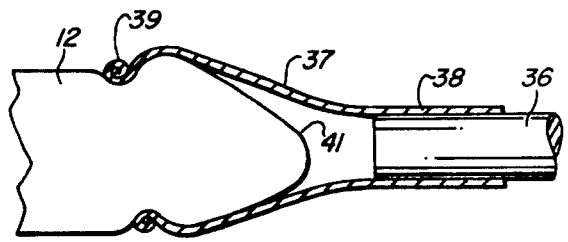
FIG. 6A is a partial cross-sectional view of the tool shown in FIG. 5 in place on the user.

This tool is used to grab the glans penis and hold the penis in an extended position by aligning the end of tool 35 with the end of shaft 12. The glans penis will penetrate into the funnel-shaped member 37, as shown in FIG. 6A. The rolled end of member 37 is then unrolled onto the glans penis sufficient distance to firmly grip it.

It should be noted that it is very difficult to apply any form of a urinary receptacle to the shaft of the penis of a human, whether young or old, since this organ is usually very pliable or flaccid. In order to accomplish such a task, it is necessary to hold the male organ in an extended position from the glans penis and, at that time, attach the urinary receptacle. Thus, tool 35 plays an important part in the proper use of apparatus 10.

Ring 11 is also provided with an adhesive surface 40 on its inner periphery which is used to grip the surface of shaft 12 of the penis when applied thereto. As noted from FIG. 6D, the slotted end of ring 11 may be tapered away from the shaft to aid in moving the flared end 44 of the funnel-shaped end 43 over it, as later explained.

In order to reduce or eliminate any irritation on the shaft of the penis at the point at which the ring is to be adhesively attached, an anti-irritant 12A may be applied to the skin of shaft 12 of the penis; one such material on the market comprises a composition employing Isopropanol, Butyl, Mono Ester and Dimethyl Phthalate.

Further, it should also be noted that the material of which ring 11 is formed should be an expandable rubber, plastic or other suitable material that has a memory and will return to its normal position after expansion. It should be formed of a low durometer material known in the trade as having a hardness A of 10 to 30. This material will not apply an undue pressure to the shaft of the penis so as to interfere with blood flow or any other normal function thereof.

OPERATION

Figure 6B:
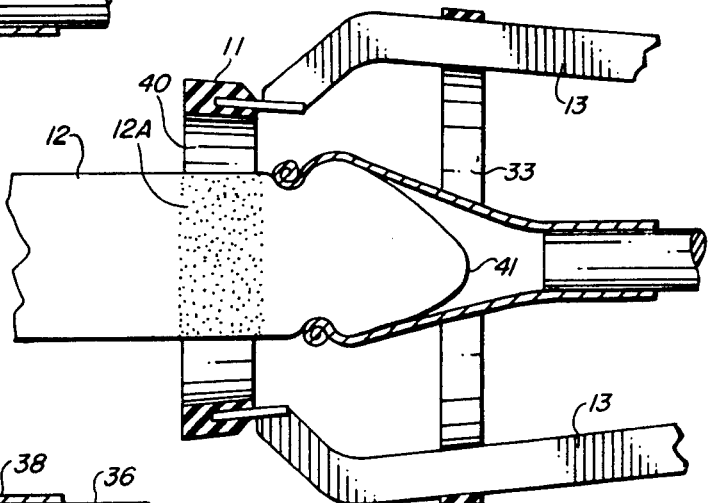
FIG. 6B is a partial cross-sectional view of the apparatus shown in FIG. 1 together with the ring shown in FIG. 4 in its ring expanded position in place over the tool shown in FIG. 6A.

In the normal procedure for applying a urinary receptacle to the shaft of the penis of a user employing the claimed invention, the user inserts fingers 19 of jaws 13 of apparatus 10 when in its unbiased condition into slots 20 of ring 11 to firmly hold the ring when it is expanded, as shown in FIG. 6B.

Ring 11 is expanded by the use of gas pressure from canister 25 to move piston 24 to the right, as shown in FIG. 2A, to spread fingers 19 away from each other.

Tool 35 is then applied to the glans penis of the user by aligning the end of tool 35 with the end of shaft 12. The glans penis should penetrate into the funnel-shaped member 37, as shown in FIG. 6A. At this point, the rolled end of member 37 is unrolled onto the glans penis a sufficient distance to firmly grip it. The user or attendant then, by means of tool 35, holds the shaft of the penis in its extended position.

With ring 11 expanded, instrument or apparatus 10 is then longitudinally moved over the free end of tool 35, with the other end of rod 36 now being attached to the user, passing through the opening between fingers 19 of jaws 13, ring 11 which is in fingers 19 and in the expanded state and through opening 22 in housing 15, as shown in FIG. 7. Apparatus 10 is moved along rod 36 until the expanded ring 11 is at a point spaced approximately a quarter of an inch from the glans penis on shaft 12 and the flared end 39 of funnel 37 of tool 35, as shown in FIG. 6B. The anti-irritant 12A is then applied around the penis at the point ring 11 is to be attached.

Figure 6C:
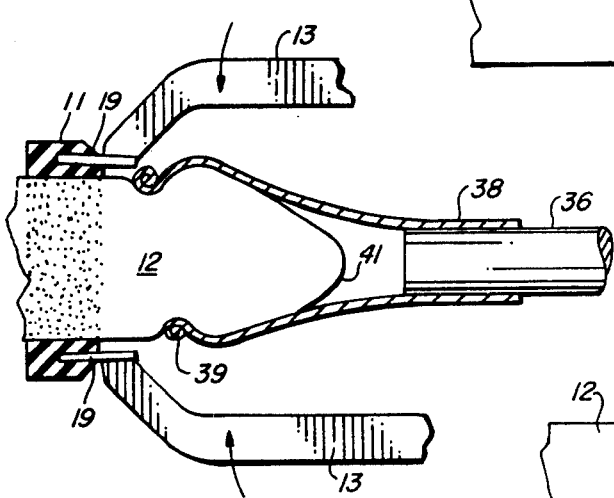
FIG. 6C is a view similar to FIG. 6B with the instrument shown in its retracted position.

The pressure is now relieved from the left side of piston 24, as shown in FIG. 2A, causing rubber bands 33 and ring 11 to bias jaws 13 to their unbiased position, which causes ring 11 to return to its original normal size. At this point, as shown in FIG. 6C, ring 11 snugly adheres to shaft 12 at a distance spaced from end 39 of funnel-shaped member 37 and inwardly along shaft 12 from its tip or end 41. Due to adhesive 40 on the inner surface of ring 11, ring 11 seals in a leakage proof condition around shaft 12 and forms a solid anchor for the receptacle.

The fingers 19 of instrument 10 are now withdrawn from slots 20 of ring 11, and the instrument is moved longitudinally over and off of tool 35. Tool 35 is then removed from the glans penis of shaft 12 by rolling up flared end 39 of funnel member 37 of the tool.

Figure 6D:
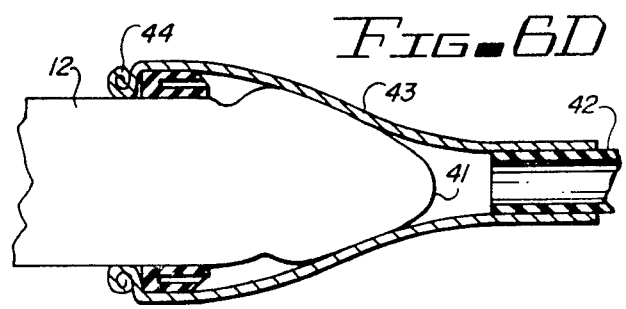
FIG. 6D is a view similar to FIG. 6A showing a drainage appliance or receptacle on the shaft of the male organ over the mounted resilient ring in a leakproof sealing arrangement.

At this point in the procedure, a drainage tube 42, which is provided with a resilient funnel shaped end 43, is applied to the end of shaft 12 in the manner shown in FIG. 6D. The flared end 44 of the funnel-shaped end 43 is expanded and applied over the glans penis 41 and over the now adhesively secured ring 13. Since the flared end 44 was biased outwardly when applied over ring 11 on shaft 12, it will snugly engage shaft 12 over and around ring 11 to form a leakproof seal with it.

If desired, a further securing means such as a piece of tape may be applied over the flared end of member 43 on the outer surface of ring 11. This is not necessary for the appliance to function effectively.

Thus, an appliance and instrument for application is provided for males having a wetting problem which will, in a leakproof manner, attach a urine receptacle to a male.

It will be apparent to those skilled in the art that changes and other modifications may be made to the apparatus shown and described herein without departing from the scope of the appended claims.

What is claimed is:

1. An annular ring for mounting on a shaft of a penis for use in attaching a urine receptacle thereto in a leakproof manner comprising:
   an elastic ring,
   said ring having a plurality of close ended slot means spacedly arranged around one end surface thereof to extend into said ring longitudinal of its length and intermediate the interior and exterior surface,
   said slot means penetrating means the body of said ring far enough so that they can receive fingers of a medical instrument which will expand said ring a predetermined amount,
   said ring being provided with an adhesive surface around its inner peripheral surface for adhering to the penile shaft.

2. The annular ring set forth in claim 1 wherein:
   said one end of said ring is tapered away from its inner periphery to aid in rolling a sheath of a urine receptacle over it when applying the receptacle to the shaft of a penis.

3. A method of attaching a urine receptacle to a penis in a leakproof manner comprising the steps of:
   provide an instrument having expansion fingers and jaws, insert the fingers into a ring having closed ended slots,
   expanding an elastic ring with the instrument, the inner peripheral surface of which is provided with an adhesive coating,
   holding the penis in an extended position,
   sliding said expanded ring over the shaft of the penis without contacting the penis, and
   relaxing the ring causing it to return to its normal condition on the shaft,
   sliding the funnel shaped end of a resilient catheter over the glans penis and said ring, and
   said end of said catheter gripping the outside end of said ring in a leakproof manner.

4. The method set forth in claim 4 in further combination with the step of:
   adding an anti-irritant to the shaft of the penis at the point on the penis at which the ring is to be secured prior to its application thereto.

* * * * *

UNITED STATES PATENT OFFICE
CERTIFICATE OF CORRECTION

Patent No. 4,484,918　　　　　　　　　Dated November 27, 1984

Inventor(s)　Herbert A. Omley

It is certified that error appears in the above-identified patent and that said Letters Patent are hereby corrected as shown below:

Claim 1, line 9, after penetrating, cancel "means."

Claim 4, line 1, cancel "4" and substitute ---3---.

Signed and Sealed this

Twenty-third Day of April 1985

[SEAL]

Attest:

DONALD J. QUIGG

Attesting Officer　　　Acting Commissioner of Patents and Trademarks